United States Patent
Almogy et al.

(10) Patent No.: US 7,969,564 B2
(45) Date of Patent: Jun. 28, 2011

(54) SYSTEM AND METHOD FOR DEFECT LOCALIZATION ON ELECTRICAL TEST STRUCTURES

(75) Inventors: Gilad Almogy, Kiriat-Ono (IL); Chris Talbot, Emerald Hills, AZ (US); Lior Levin, Cupertino, CA (US)

(73) Assignee: Applied Materials Israel, Ltd., Rehovot (IL)

( * ) Notice: Subject to any disclaimer, the term of this patent is extended or adjusted under 35 U.S.C. 154(b) by 1369 days.

(21) Appl. No.: 10/530,157

(22) PCT Filed: Oct. 3, 2003

(86) PCT No.: PCT/US03/31398
§ 371 (c)(1),
(2), (4) Date: Mar. 13, 2006

(87) PCT Pub. No.: WO2004/031791
PCT Pub. Date: Apr. 15, 2004

(65) Prior Publication Data
US 2006/0192904 A1 Aug. 31, 2006

Related U.S. Application Data

(60) Provisional application No. 60/416,333, filed on Oct. 3, 2002.

(51) Int. Cl.
*G01N 21/00* (2006.01)
(52) U.S. Cl. ............ 356/237.2; 382/145; 382/128; 382/112; 382/149; 257/72; 257/48; 356/237.1; 438/15; 438/16; 438/14

(58) Field of Classification Search .................. None
See application file for complete search history.

(56) References Cited

U.S. PATENT DOCUMENTS

| | | | |
|---|---|---|---|
| 5,272,434 A | 12/1993 | Meyrueix et al. | |
| 5,394,098 A | 2/1995 | Meyrueix et al. | |
| 5,699,447 A * | 12/1997 | Alumot et al. | 382/145 |
| 6,271,671 B1 * | 8/2001 | Charles et al. | 324/753 |
| 6,403,386 B1 | 6/2002 | Liu | |

FOREIGN PATENT DOCUMENTS

| | | |
|---|---|---|
| EP | 0 493 906 A1 | 7/1992 |
| EP | 0 299 432 A2 | 1/1993 |

OTHER PUBLICATIONS

"What is a lock-in Amplifier" Perkin Elmer Technical note, 2000.*
"Explore the Lock-in Amplifier" EG&G Princeton Applied Research, 1983.*
Applied Materials Israel, Ltd.; CN Application No. 200380101404.X; Office Action dated Sep. 7, 2007; 21pp.
Applied Materials Israel, Ltd.; CN Application No. 200380101404.X; Office Action dated Jun. 27, 2008; 6pp.
International Search Report, PCT/US2003/031398, Mar. 19, 2004, 6pp.

* cited by examiner

*Primary Examiner* — Sally A Sakelaris
(74) *Attorney, Agent, or Firm* — SNR Denton US LLP

(57) ABSTRACT

A method and system for defect localization includes: (i) receiving a test structure that includes at least one conductor that is at least partially covered by an electro-optically active material; (ii) providing an electrical signal to the conductor, such as charge at least a portion of the conductor; and (iii) imaging the test structure to locate a defect.

7 Claims, 15 Drawing Sheets

Probe Pads 20  Short Defect 22

10

Probe pads 20   Open defect 24

11

Floating comb Fingers 26

Short defect 28

12

Without transparent conductive layer on top to increase E field strength.

502

602

SYSTEM AND METHOD FOR DEFECT LOCALIZATION ON ELECTRICAL TEST STRUCTURES

CROSS-REFERENCES TO RELATED APPLICATIONS

The present patent application is a national phase application of International Application No. PCT/US03/031398 filed Oct. 3, 2003, which claims priority from U.S. Provisional Application No. 60/416,333 filed Oct. 3, 2002.

FIELD OF THE INVENTION

This invention relates to methods and systems for defect localization and especially for defects, including both hard defects and soft defects, that occur within electrical test structures used in microfabrication.

BACKGROUND

Test structures are fabricated in order to enhance defect detection and/or analysis of a microfabrication manufacturing process. Test structures may be included in a variety of objects, such as but not limited to integrated circuits, masks (for fabricating integrated circuits, flat panel displays and the like), MEMS devices and the like. They may be located at various locations on these objects, such as in the integrated circuit die or in scribe lines on semiconductor wafers. In many cases the size of a defect is much smaller than the size of the test structure and there is a need to locate the defect within the test structure in order to perform classification and root cause analysis. The localization of the defect is difficult and time consuming, especially in the context of integrated circuit manufacturing, and failure analysis devices, such as Defect Review Scanning Electron Microscope (DR-SEM) that are utilized during said manufacturing process.

Usually, test structures include one, two or more electrical conductors that may be shaped in various manners, such as a comb, serpentine, nest, via chain and the like that are known in the art. A defective test structure may be characterized by hard defects (electrical short or electrical open, i.e. isolated) and soft defects (high resistance vias or shorts resulting from metal threads or stringers).

PCB electro-optic high speed sampling-based probing of voltages on PCBs is known as described for example in US patents to Paul Meyreueix et al of Schlumberger U.S. Pat. No. 5,272,434 and U.S. Pat. No. 5,394,098. An electro-optic (EO) coating is applied to a PCB and is then used to sense and sample the voltage waveform as a function of time on PCB conductors under the EO coating.

The Microloop Product by KLA-Tencor of San Jose Calif. uses a combination of the KLA-Tencor eS20 e-beam inspection system and KLA-Tencor eV300 DR SEM for non-contact inspection, defect localization and classification of defects in electrical test structures. Microloop cannot detect or localize soft defects as the beam induced current (typically <100 nA and often <1-10 nA) through a high resistance defect often does not result in a sufficient voltage difference across the defect for that voltage difference to be detected in a voltage contrast image. Microloop is also prohibitively expensive for some manufacturers to employ routinely due to the cost and complexity of the vacuum and loadlock systems required by the DR and EBI SEMs.

Alternately a voltage contrast e-beam prober, for example, an IDS 10000 e-beam prober from NPTest of San Jose, Calif. (formerly Schlumberger Semiconductor Solutions) with mechanical probes or a probecard in the vacuum chamber, can, using direct electrical connections (with mechanical probes or probecard), inject larger currents (than are possible with e-beam) into test structures. The larger current when passing through a soft electrical defect produces a larger voltage and therefore a larger voltage contrast signal that can be more readily detected. However, mechanical probes are difficult to manipulate accurately or reliably inside a vacuum chamber and generate micro-particle contamination that is unacceptable in cleanroom tools, particularly in-line SEMs (DR, EBI & CD) and generally in microfabrication manufacturing.

OBIRCH—Optical Beam-Induced Resistance CHange—Nikawa-san of NEC publications at ISTFA and IRPS 1999 and 2000: an optical beam is raster scanned over the structure and the supply current or voltage is monitored. The optical beam (usually IR) heats the structure locally, and temporarily increasing the resistance of the element heated. When a defective high resistance structure is heated, the resistance change is often greater and results in a larger and readily detectable change of supply current (or voltage or in the case of a constant current supply). An OBRICH image can be produced by plotting the change in supply current or voltage against the position of the optical beam in the raster—defects show as bright (or dark) areas in the image corresponding with the larger change in current or voltage induced by the presence of the defect.

SUMMARY OF THE INVENTION

The invention provides methods and system for cost-effectively and efficiently localizing defects including both soft defects and hard defects in test structures (and other structures), especially without using cumbersome and expensive vacuum chambers and associated pumping systems.

The invention provides a method for defect localization in a microfabricated test structure (and other structures) based upon optical inspection of optical signals that represent the electrical status of the test structure.

The invention provides a defect localization method that includes: (i) receiving a test structure that comprises at least one conductor and an electro-optically active material that is positioned such as to provide an indication about the electrical status of at least one or more of the conductors of the test structure; (ii) providing an electrical signal to the conductor and (iii) imaging the test structure to locate a defect.

The invention provides a system for defect localization that includes: (i) means for providing an electrical signal to at least one conductor of a test structure, wherein the test structure comprises at least one conductor and an electro-optically active material that is positioned such as to provide an indication about the electrical status of one or more of the conductors of the test structure; (ii) means for illuminating the test structure; (iii) at least one detector, for detecting light scattered or reflected from the test structure; and (iv) a processor for processing detection signals from the detectors to locate a defect.

The invention provides a test structure that includes at least one conductor configured to receive an electrical signal and an electro-optically active layer positioned such as to at least partially interact with at least one conductor, such as to provide an optical indication about the electrical state of the at least one conductor. The test structure may further include a non-opaque conductive material positioned such as to enhance detected radiation from the test structure.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION

In the following detailed description of the preferred embodiments and other embodiments of the invention, reference is made to the accompanying drawings. It is to be understood that those of skill in the art will readily see other embodiments and changes may be made without departing from the scope of the invention.

The term "electro-optically-active" material relates to a material that emits light or that transmits or reflects light differently in response to an electrical state of the material or an electric field applied to the material. The intensity of the emitted light can be responsive to a voltage potential of the material.

Figure 1A:
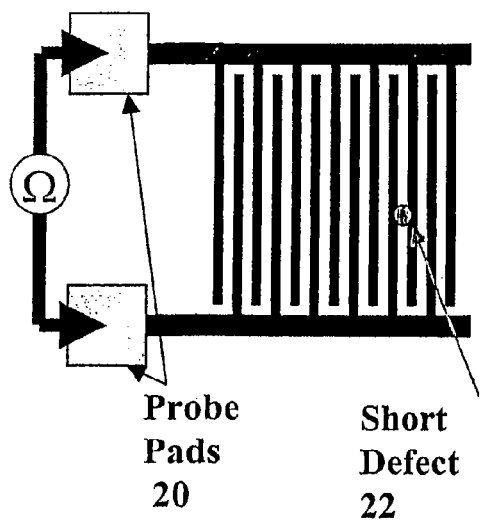
FIGS. 1a-1c illustrate prior art test structures and pads used to probe the test structures.

FIG. 1 depicts prior art test structures. FIG. 1A depicts a comb structure 10 that includes an interdigitated fingers structure connected to probe pads 20 that are connected to an ohmmeter. Structure 10 is commonly used for detecting electrical short-type defects such as metal stringers. An electrical short, such as short 22, between any two fingers is readily detected by electrically measuring the resistance between the two interdigitated comb structures. Such shorts can also be detected using beam induced voltage contrast when one side of the comb is electrically floating and the other side is electrically grounded. However, it is not possible with this structure to localize the defect with voltage contrast. When a short defect in a comb is undetectable using inspection methods, it is extremely difficult and time consuming to localize the precise location of the defect for root cause analysis or classification.

Figure 1B:
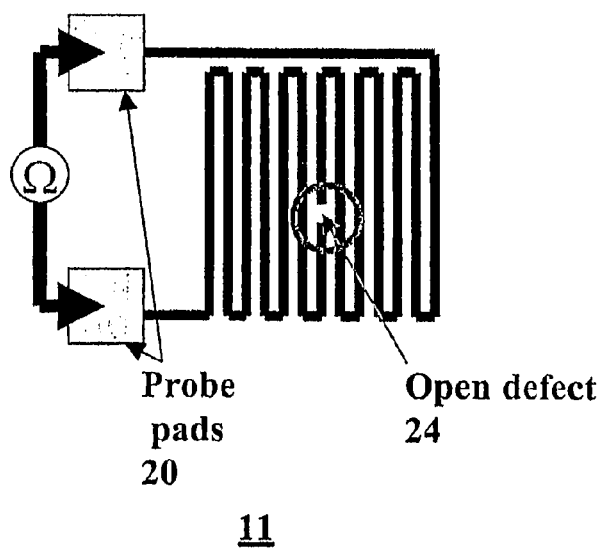

FIG. 1B depicts a prior art test structure 11 that has a serpent structure that typically includes a chain of vias between two metal layers. Each of the two ends of the serpent structure is connected to probe pads 20 that in turn are connected to an ohmmeter. An electrical open defect, such as open defect 24, can readily be detected by an electrical test of the structure. Localization of these defects can be accomplished using the methods depicted in FIGS. 2a and 2b. However, if the open defect is not characterized by a very high resistance or is completely open, localization is very difficult even with beam-induced voltage contrast as the beam induced current through a high resistance defect often does not result in a sufficient voltage difference across the defect for that voltage difference to be detected by voltage contrast.

Figure 1C:
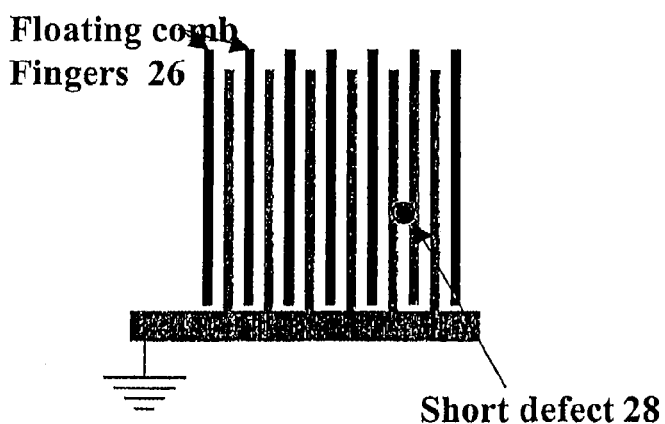

FIG. 1c depicts prior art test structure 12 that includes a one-sided comb with floating comb fingers 26 designed to enhance localization with beam-induced voltage contrast (BIVC). KLA-Tencor's Microloop product uses a similar one sided comb-like test structure where one side of the comb is comprised of electrically isolated fingers. This approach facilitates localization of a short defect, such as defect 28, to a particular pair of fingers in the comb but further inspection is required to localize the defect itself. Open defects can be detected but only in the grounded comb fingers. This structure is also limited because the resistance of the short defect is typically unknown with the BIVC method (and no pads exist for electrical test) and hence it is very difficult to know if a defect is a nuisance defect as for example would be the case for a 10 M ohm metal stringer in a logic circuit. Conversely a high resistance open defect (10-10 M+ ohms) in the grounded comb fingers will not be detected with voltage contrast. If the short defect cannot be detected by inspection, localization remains difficult and slow.

Figure 2A:
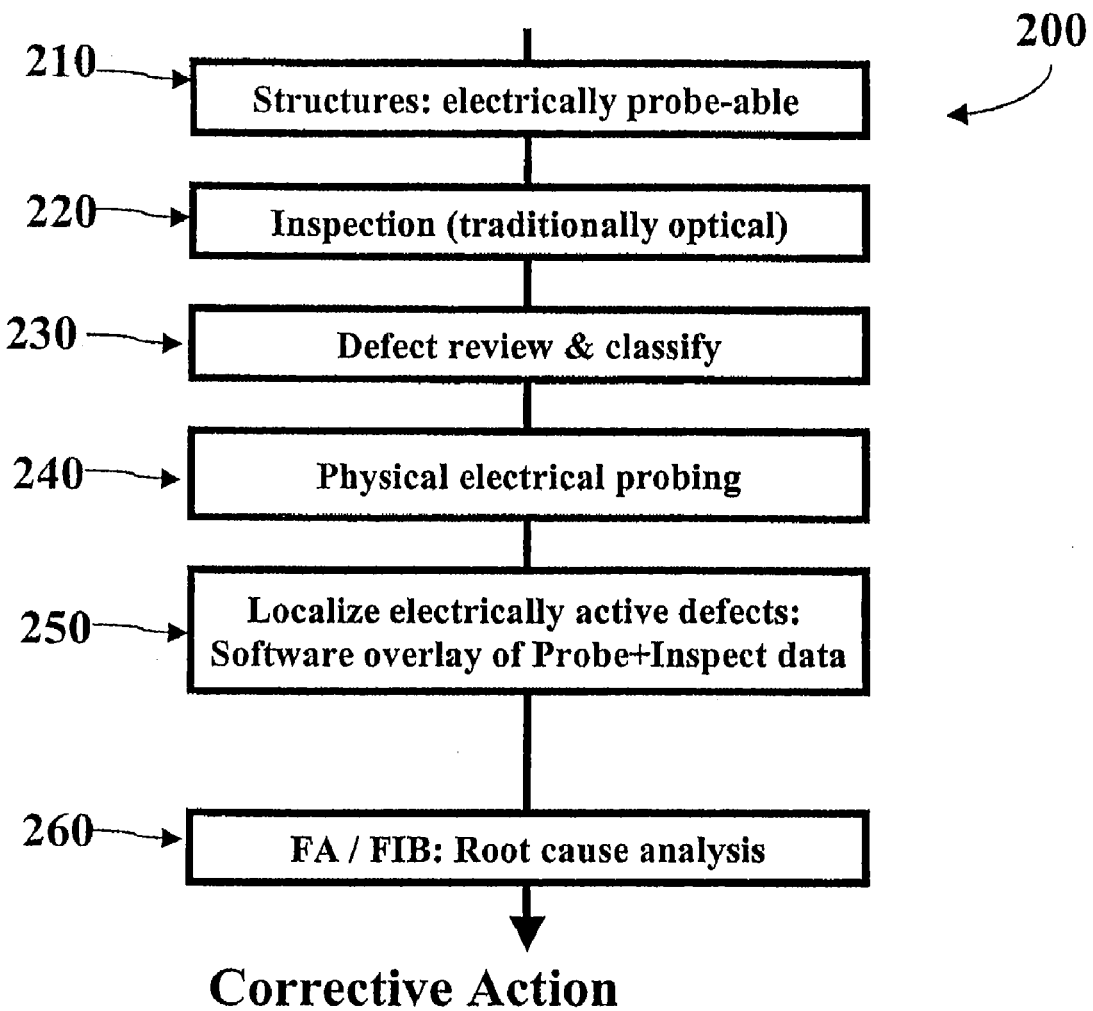
FIG. 2a is a prior art method for examining a test structure.

FIG. 2a is an example test structure electrical defect detection localization method flow diagram. Method 200 includes step 210 of providing a structure that can be inspected by a probe based inspection method, step 220 of inspecting the structure, typically using an optical based inspection method, to detect visible defects, step 230 of performing visible defects-review and classification, steps 240 and 250 of performing a probe based test, while using visible defect information gained from previous steps as well as from conventional electrical tests, and step 260 of cross sectioning the structure to further evaluate the status of the structure. The principle limitation of method 200 is that it cannot be used to locate defects that cannot be detected by inspection—which is increasingly a problem for optical inspection tools and for subsurface electrical defects such as high resistance contacts and vias.

Figure 2B:
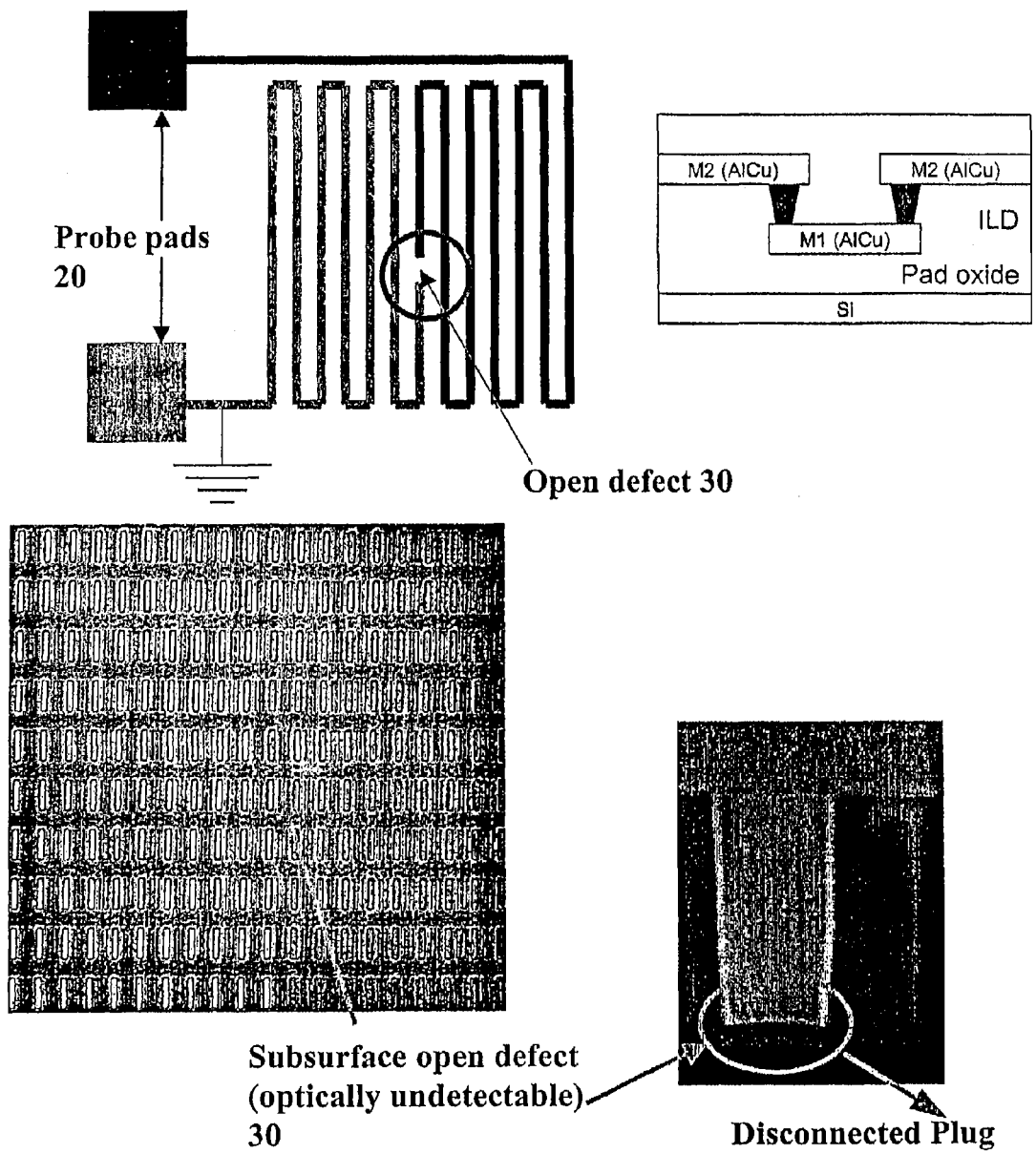
FIG. 2b illustrates a prior art defective test structure that is not located by prior art optical inspection methods.

FIG. 2B is a graphical illustration of an exemplary prior art localization technique using beam-induced SEM or e-beam voltage contrast (BIVC). In this example, an electron beam first charges part of a test structure which then appears with a different contrast due to the different voltage induced on the floating portion of the structure. Note that one end of the structure can be grounded to enhance contrast between the two halves of the structure although in some circumstances effective localization can be achieved without grounding. A limitation of this approach is that high resistance vias prevent this differential charging effect as the charge is conducted through the high resistance via faster than the beam can be used to interrogate the structure for voltage differences.

Figure 3A:
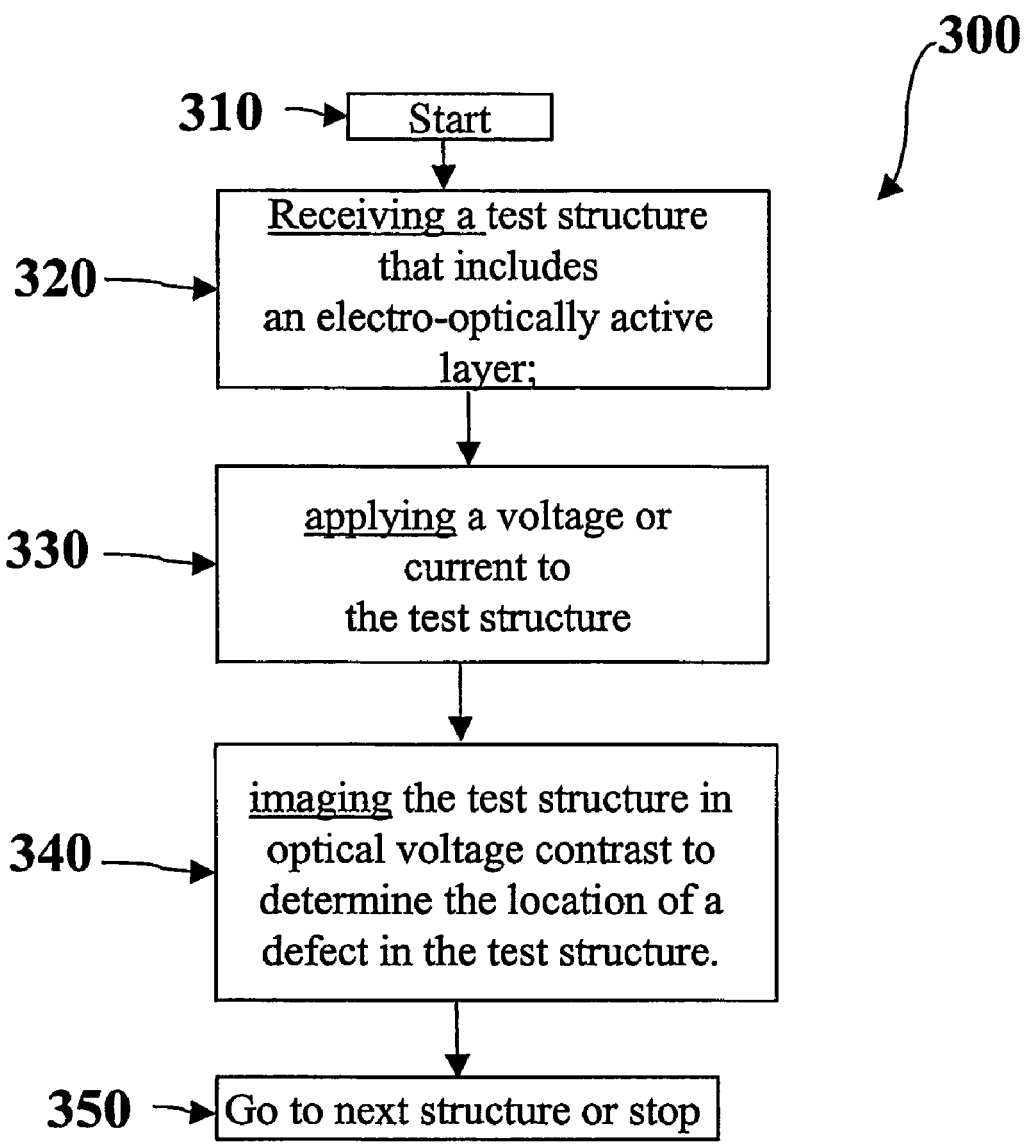
FIGS. 3a, 3b, 7 and 8 are flow charts of several methods for defect localization, according to various embodiments of the invention.

FIG. 3A is a flow diagram of a method 300 of an embodiment of the invention for localizing a defect in a test structure (and other structures) in an optical voltage contrast mode. Method 300 includes: "start" step 310, step 320 of providing a test structure that includes an upper electro-optically active layer, step 330 of applying a voltage or current to the test structure (collectively applying an electrical signal that can include using a voltage source, current source or combination thereof or applying charge or an electrical signal to charge at least a conductor portion of the test structure), step 340 of imaging the test structure in optical voltage contrast mode to determine the location of a defect in the test structure. The method can be repeated for multiple test structures (as indicated by step 350 "go to next structure or stop loop").

Figure 5A:
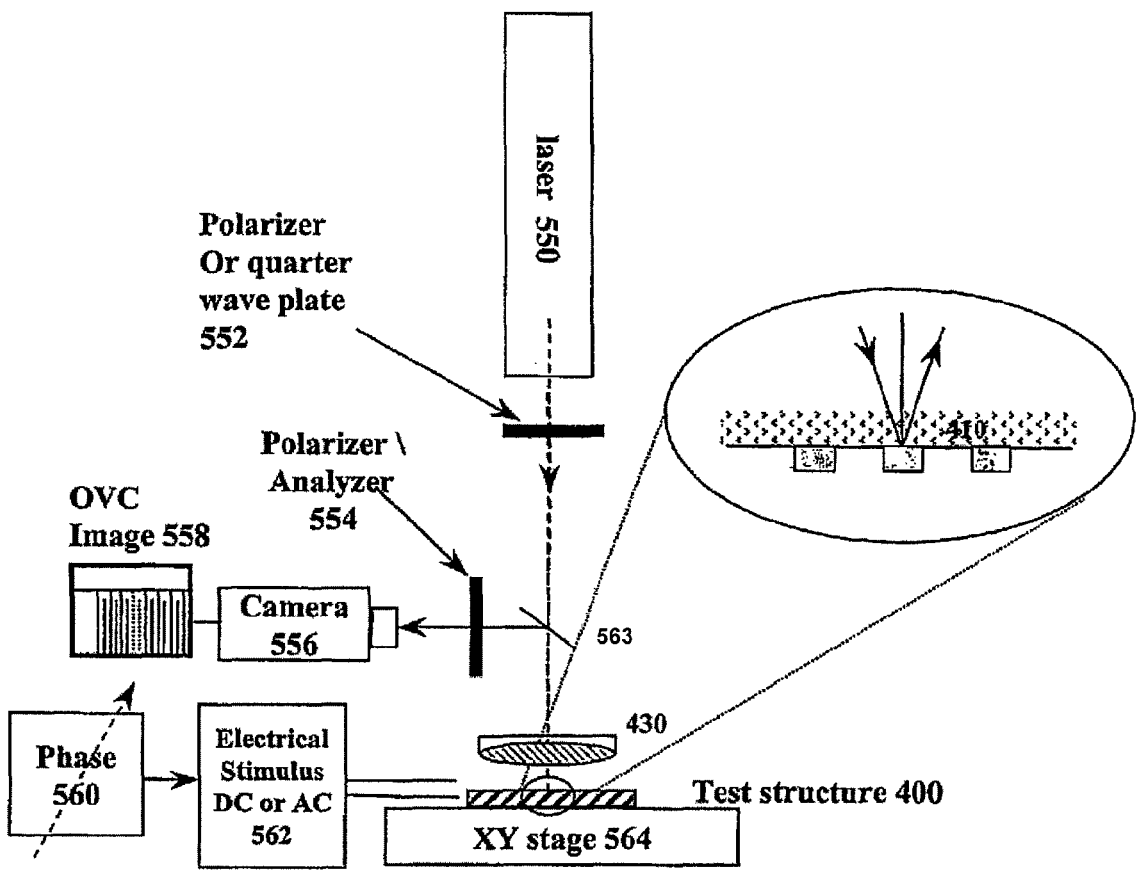
FIGS. 5a and 5b illustrate systems for defect localization, according to various embodiments of the invention.
Figure 5B:
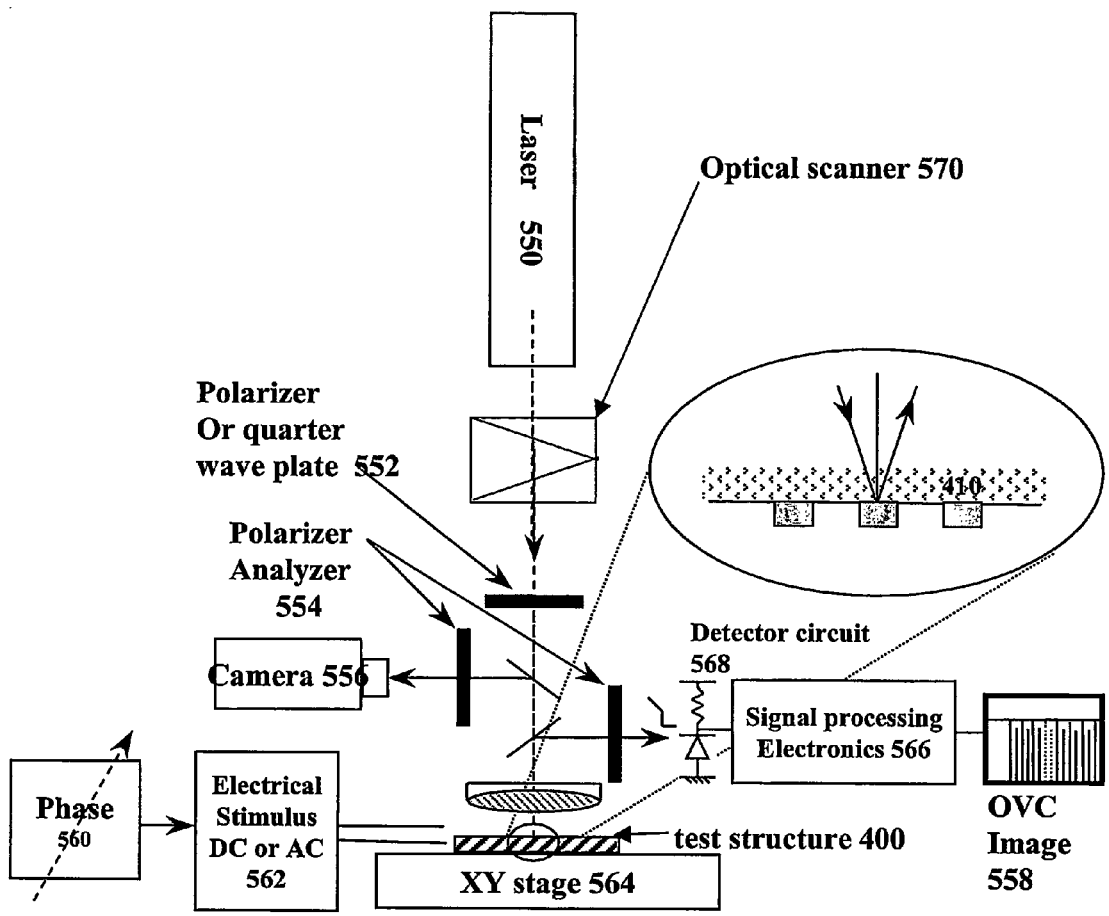

The electro-optically active layer can be made of materials such as a liquid crystal or a birefringent material (preferably electro-optically active polymers). Optionally, the electro-optically active layer is coated with a non-opaque (transparent, semi-transparent or translucent) conductive layer. Step 340 of imaging may include illumination with polarized light optionally from a laser light source as depicted in FIGS. 5A-5B.

Figure 3B:
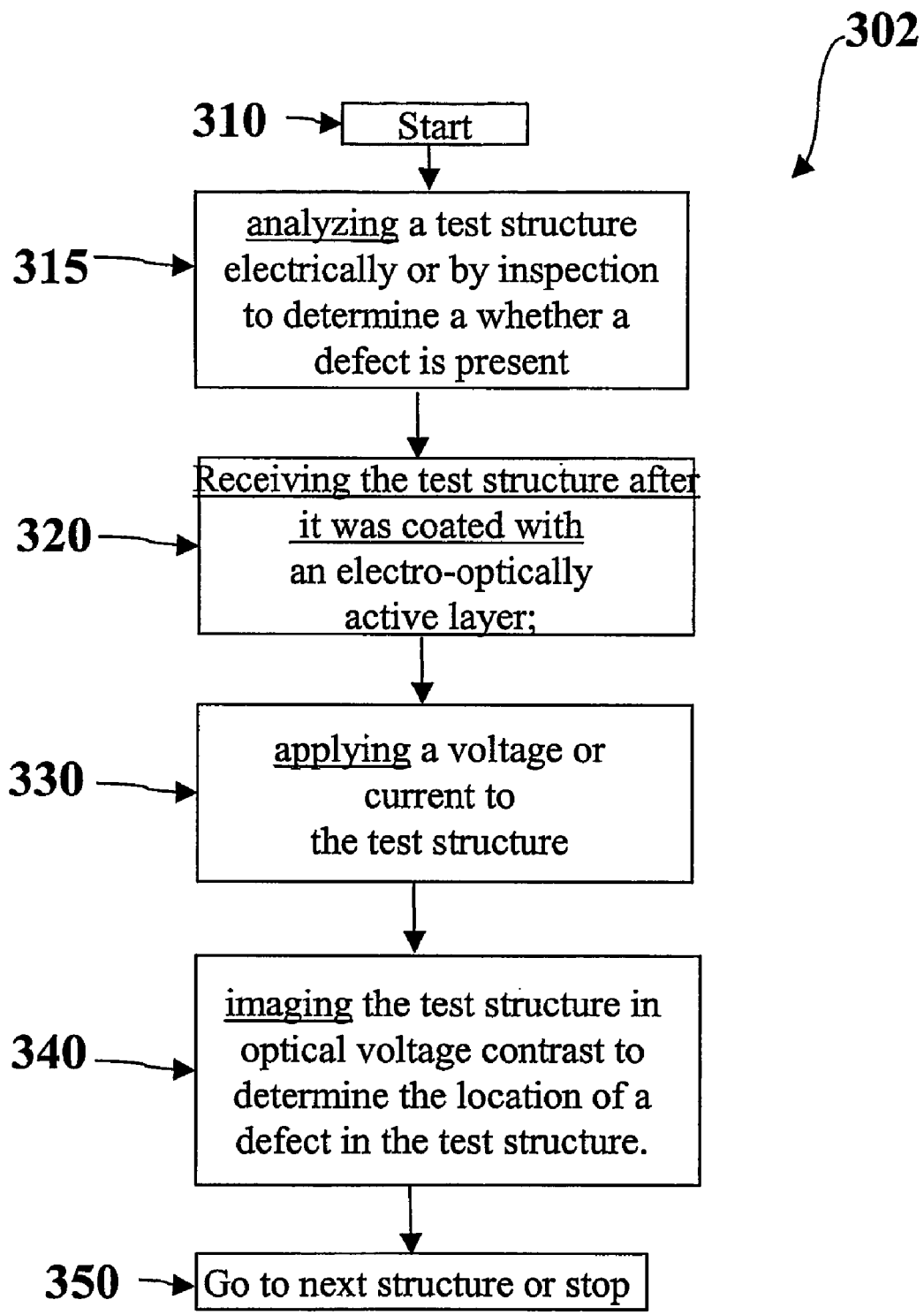

FIG. 3B is a flow diagram of a method 302 for localizing a defect in a test structure. Method 302 includes steps 310 ("start"), 320-350 of method 300 and an additional step 315 that precedes step 320. Step 315 includes analyzing a test structure that does not include the electro-optically active layer, by a prior art inspection method, such as those mentioned above, including an optical inspection and electrical testing to locate defects. These defects may be later imaged during step 340, although step 340 includes inspection of other areas of the test structure, to locate defects that were not located during step 315.

Figure 4A:
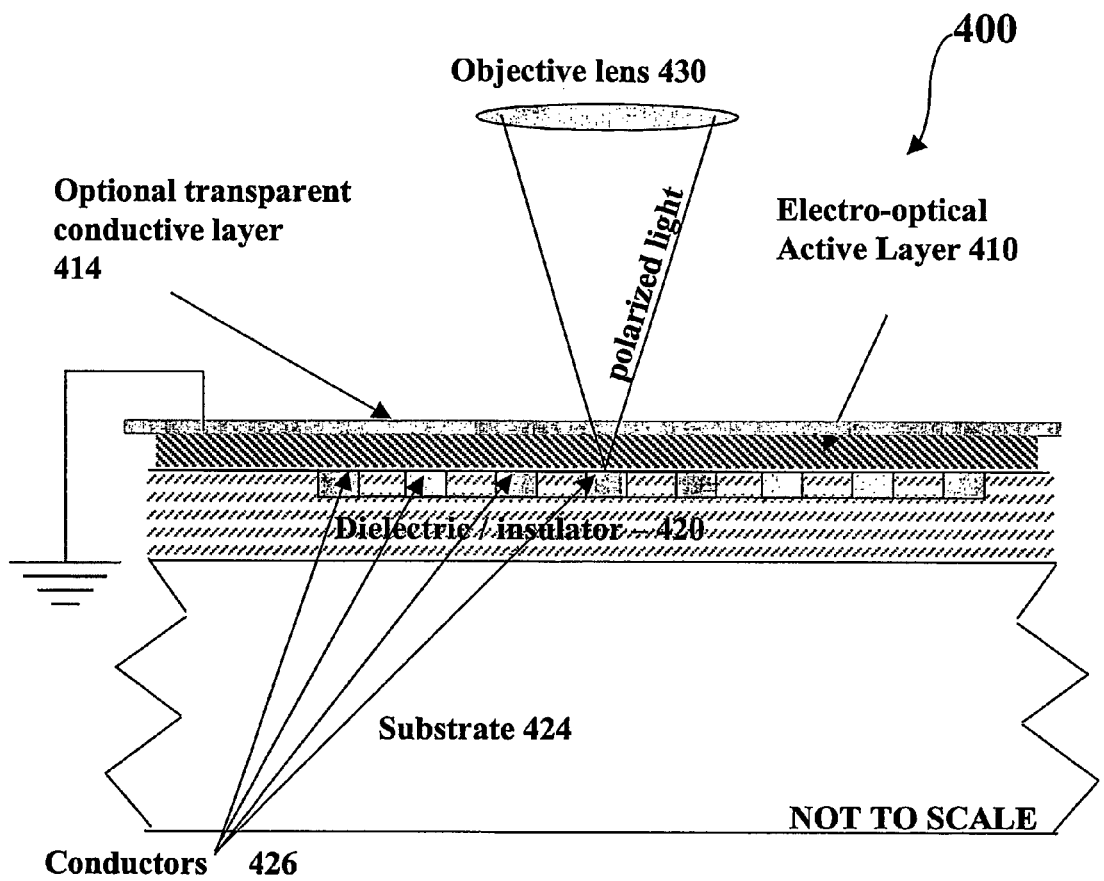
FIG. 4a illustrates a test structure that includes an electro-optically active layer.

FIG. 4a depicts a test structure 400 that includes a substrate 424 (typically made of silicon), a dielectric insulator layer 420 located above the substrate, multiple conductors 426 that form the conductive part of the test structure (typically made of copper or aluminum) that are partially surrounded by the dielectric insulator layer 420. The upper surface of the dielectric insulator layer 420 as well as the conductors 426 are coated with electro-optic layer 410, that in turn is located beneath an optional transparent or semitransparent conductive layer 414. The functionality of the conductive layer 414 is further described at FIG. 4c. It is mainly used for increasing the E-field within electro-optic layer 410 being induced by the provision of voltage to conductors 426 of the test structure 400. It is noted that when using copper conductors, there is a need to add a temporary layer of passivation to the test structures to prevent rapid corrosion of the copper. The electro-optic layer 410 in many circumstances can also suffice as a temporary passivation layer to prevent or delay this undesirable corrosion.

Figure 4B:
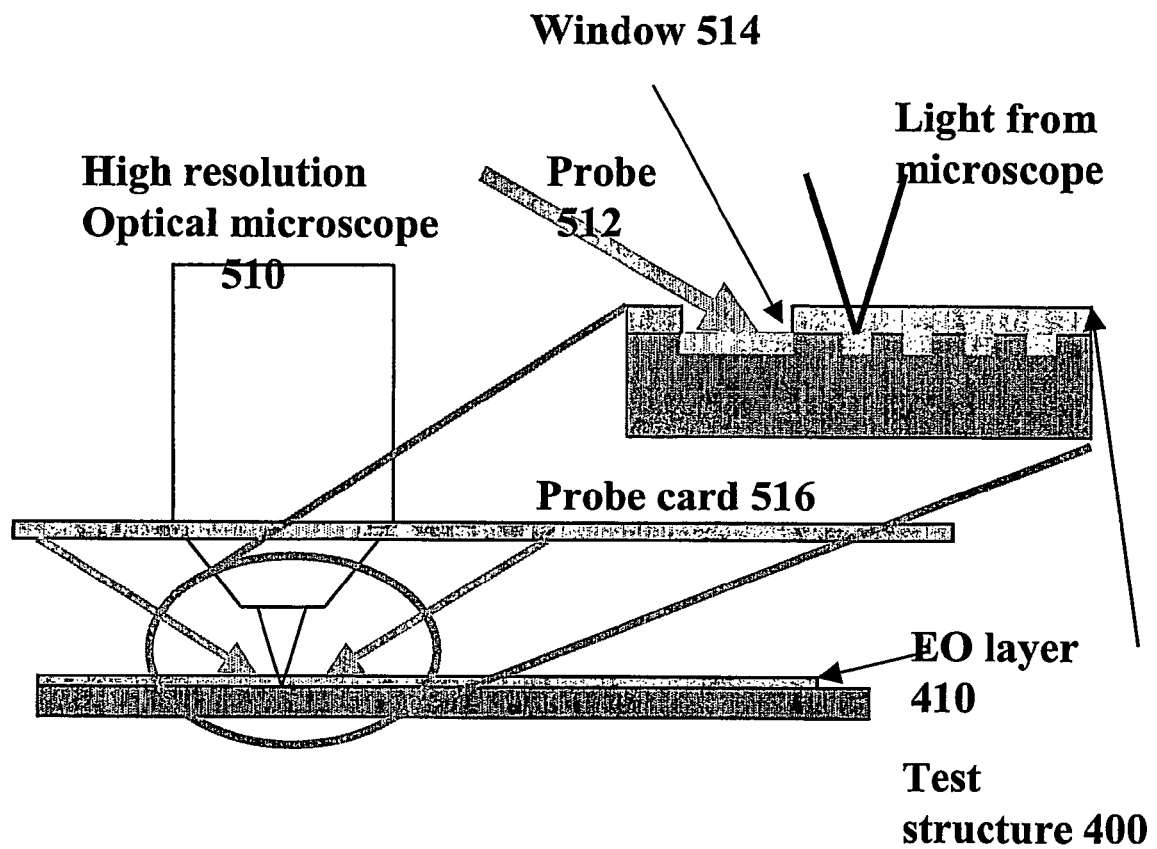
FIG. 4b depicts a system for defect localization as well as a test structure, according to an embodiment of the invention.

FIG. 4b depicts in more detail the arrangement of a high resolution optical microscope for imaging and detecting defects, as well as a test structure that includes an electro-optic layer such as layer 410. A high resolution optical microscope 510 is positioned such as to direct light towards a test structure 400 and to receive light reflected or scattered from said test structure. In addition, probe based measurements are facilitated by providing a probe card 516 that may be connected to probes such as probe 512 that may contact a conductive pad that is positioned below a window within the electro-optical layer 410 (as well as the conductive layer 414). FIG. 4b describes a probe 512 that can contact the conductors of the test structure 400. Optical microscope 510 and probe card 516 may be connected to a processor (which may be included within the microscope) that is capable of receiving optical detection signals from microscope 510 and electrical signals from card 516 and processing said signals to locate a defect. The system usually generates an image, but this is not necessarily so.

Figure 4C:
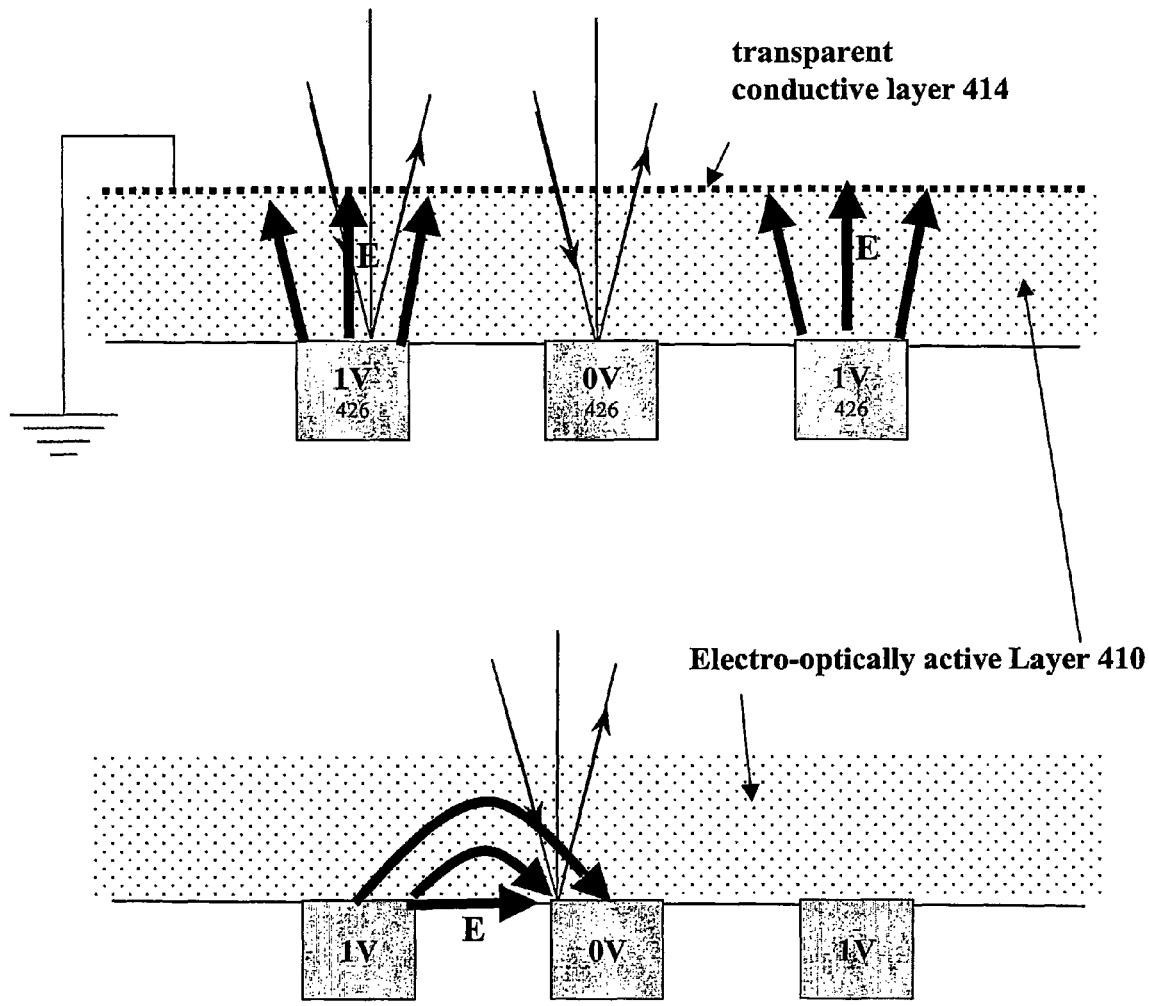
FIG. 4c illustrates an electric field within the electro optically active layer with and without an optional transparent conductive layer, according to an embodiment of the invention.

FIG. 4c illustrates the electric field within the electro-optic layer with and without an the optional transparent or semitransparent conductive layer 414 of test structure 400. This layer prevents the leakage of an electrical field flux from one conductor 426 to another and increases the amount of flux that is directed outside the test structure. The Figure also describes the potential of each of the three conductors. While the provision of a conductive layer adds processing complexity, it provides a stronger E field over the surface of the structure.

FIG. 5a depicts an optical system 500 as well as an inspected test structure, such as test structure 400 of FIG. 4a that includes an upper electro optical layer 410 and optionally a conductive layer 414. An optical microscope is used for imaging the test structure, and FIG. 5a illustrates some of the components of said microscope.

Optical system 500 includes means for providing an electrical signal such as electrical stimulus unit 562 and even phase unit 560; means for illuminating the test structure, such as laser 550, polarizer or quarter wave plate 552, beam splitter 563 and objective lens 430; at least one detector, such as camera 556 and a processor (not shown) for processing signals from the at least one detector, and can also coordinate the operation of various parts of optical system 500. The processor may analyze the signals to provide the location of a defect (by tracking the changes in color of the image, in response to the shape of the conductors of the test structure), but this is not necessarily so and once an image is provided to a user, the user can determine the location of the defect.

An XY stage 564 provides for moving the test structure 400 relative to the microscope to allow imaging of the complete test structure 400 and for moving between test structures. The system may also have z-axis movement capabilities for functions including focusing manipulating the probecard. Electrical stimulus is provided to the test structure (via pads that are connected to the conductors 426 of the test structure 400) by electrical stimulus unit 562. The electrical stimulus can be DC or AC and the phase of the AC can optionally be adjusted or synchronized, by phase unit 560, with the camera 556.

A light source, preferably polarized and preferably a laser 550 passes through a polarizer 552 and a beam splitter 563 before entering an objective lens 430. Light returned from the test structure 400 is reflected by the beam splitter 563 through a polarizer/analyzer 554 and into a CCD camera 556 for image capture. The intensity in the image is a function of orientation of the polarizer/analyzer 554 and any change in polarization to the incident light induced by the electro-optic material layer on the test structure surface. An E field in the active electro-optic layer 410 induced by a voltage provided to the test structure by electrical stimulus unit 562, will proportionately alter the polarization state of reflected light from the test structure 400. The polarizer/analyzer 554 can be rotated to maximize the change in intensity or sensitivity seen in acquired image. A defect will appear as either a light or dark region in the acquired and displayed image, as illustrated in FIG. 6. The acquired image can be stored, displayed (the display image is denoted OVC—Optical Voltage Contrast image 558), manipulated to enhance contrast or to automatically locate the defect.

FIG. 5B illustrates system 502 and test structure 400. System 502 images test structures 400 in OVC mode. System 502 has a scanner 570 positioned downstream of the light source 550, and includes a detector 568 and sensitive signal-processing electronics 566. The optical setup is similar to that of system 500 but further includes the optical scanner 570, a second beam splitter 563, an additional polarizer/analyzer 554, a detector 568 and signal processing electronics 566 for enhancing the sensitivity of the system.

Optical scanning of a finely focused light spot is accomplished with an optical scanner 570 that includes piezo activated mirrors or prisms or similar scanning capability. System 502 can implement confocal laser scanning microscopy to enhance resolution and contrast in the resulting OVC image. An optional separate optical path is provided with a CCD camera 556 for purposes of setup, focus and alignment.

The focused spot of light passes through the microscope objective 430 to the test structure 400. Its polarization state is changed in proportion to the E field in the EO layer 410 on the test structure 400. The reflected light is further reflected by a beam splitter 563 through a polarizer/analyzer 554 and into a sensitive light detector circuit 568 that is illustrated as a light sensitive diode connected to a resistor. The detector circuit 568 may include a photo diode (PN, PIN, Avalanche etc.) or a Photo Multiplier Tube. Sensitive signal processing electronics 566 is used to extract the resulting signal from the noise. Preferred signal processing techniques include phase sensitive rectification or amplification in appropriate phase with either a chopped optical beam (chopper not shown) or in appropriate phase to an AC stimulus to the test structure. An OVC image 558 of the coated test structure is constructed by raster scanning the light spot over the structure.

Figure 6A:
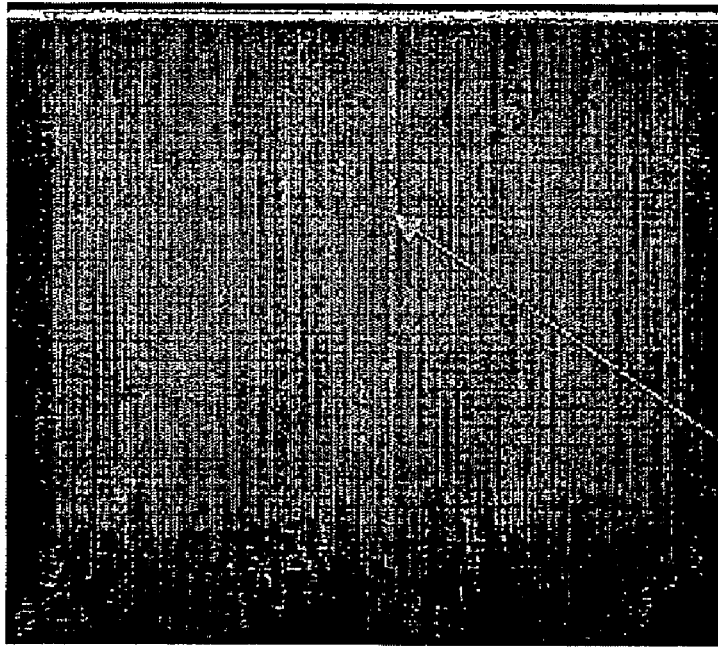
FIG. 6a is an image of a defective test structure, the image acquired during optical voltage contrast mode, according to an embodiment of the invention.

FIG. 6a is an illustration of optical image 602 showing a defect 604 in OVC mode in a fine comb structure. The defect is located along the bright line. Note that even though the resolution of this image is insufficient to show the individual features of the test structure, the defect signature is still clearly visible.

Figure 6B:
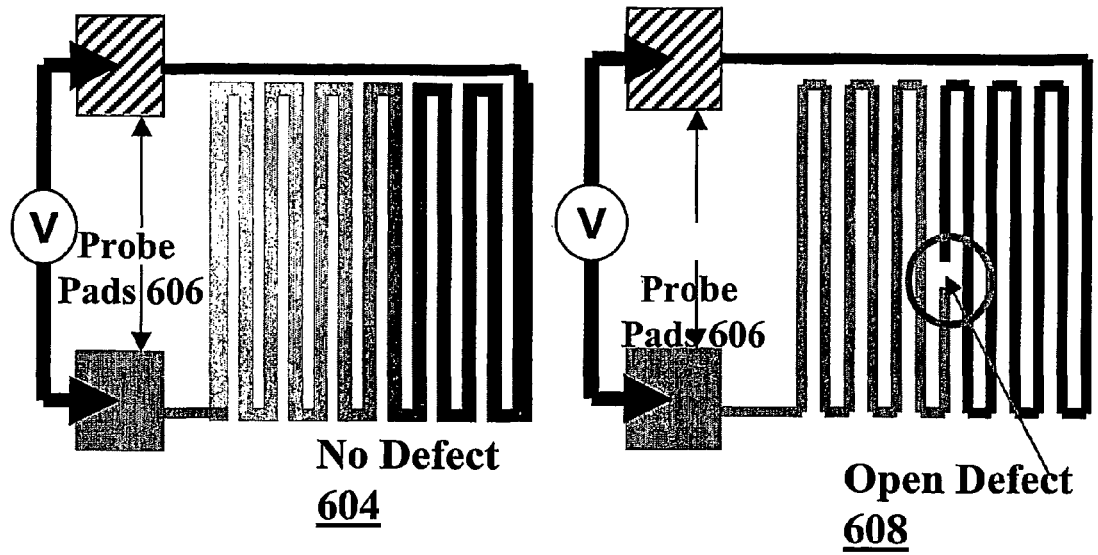
FIG. 6b depicts images of a non-defective test structure as well as of two defective test structures, according to an embodiment of the invention.
Figure 6B:
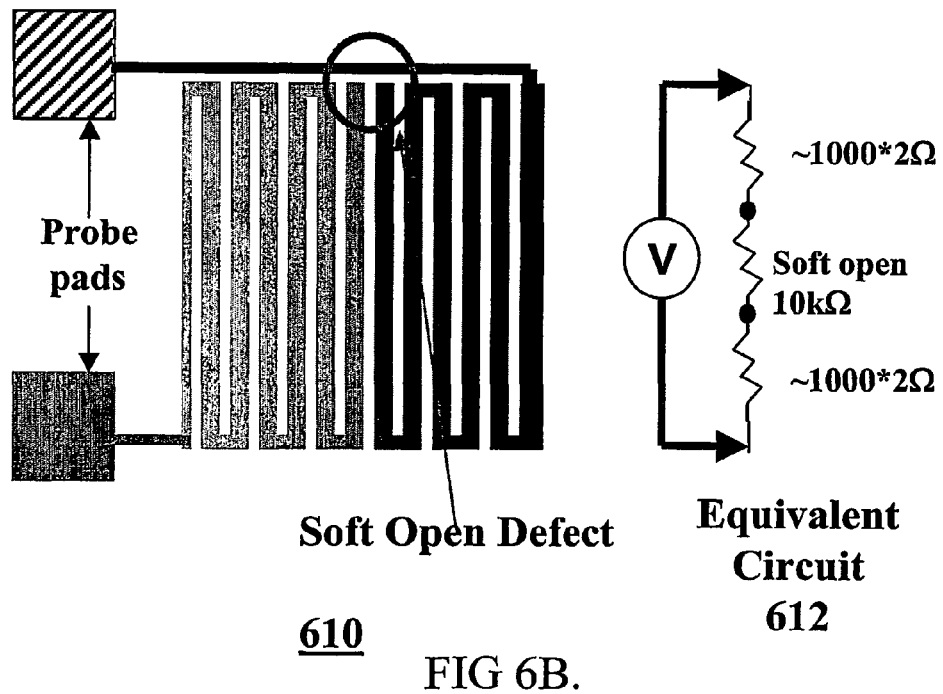

FIG. 6b illustrates OVC images of test structures. Image 604 illustrates probe pads 606 connected to two ends of a non-defective test structure 400. The color (gray scale) of the test structure monotonically increases from the lower end to the upper end. Image 608 illustrates probe pads 606 connected to two ends of a defective test structure (e.g. 400) that includes an open defect. Due to the open defect there is a difference between the gray level of conductors positioned at both sides of the open defect. Image 610 illustrates probe pads 606 connected to two ends of a defective test structure 400 that includes a soft open defect (a high resistance of about 10 kohm, as illustrated by equivalent circuit 612). Due to the soft open defect there is a graded difference between the gray levels of conductors positioned at both sides of the soft open defect.

Figure 7:
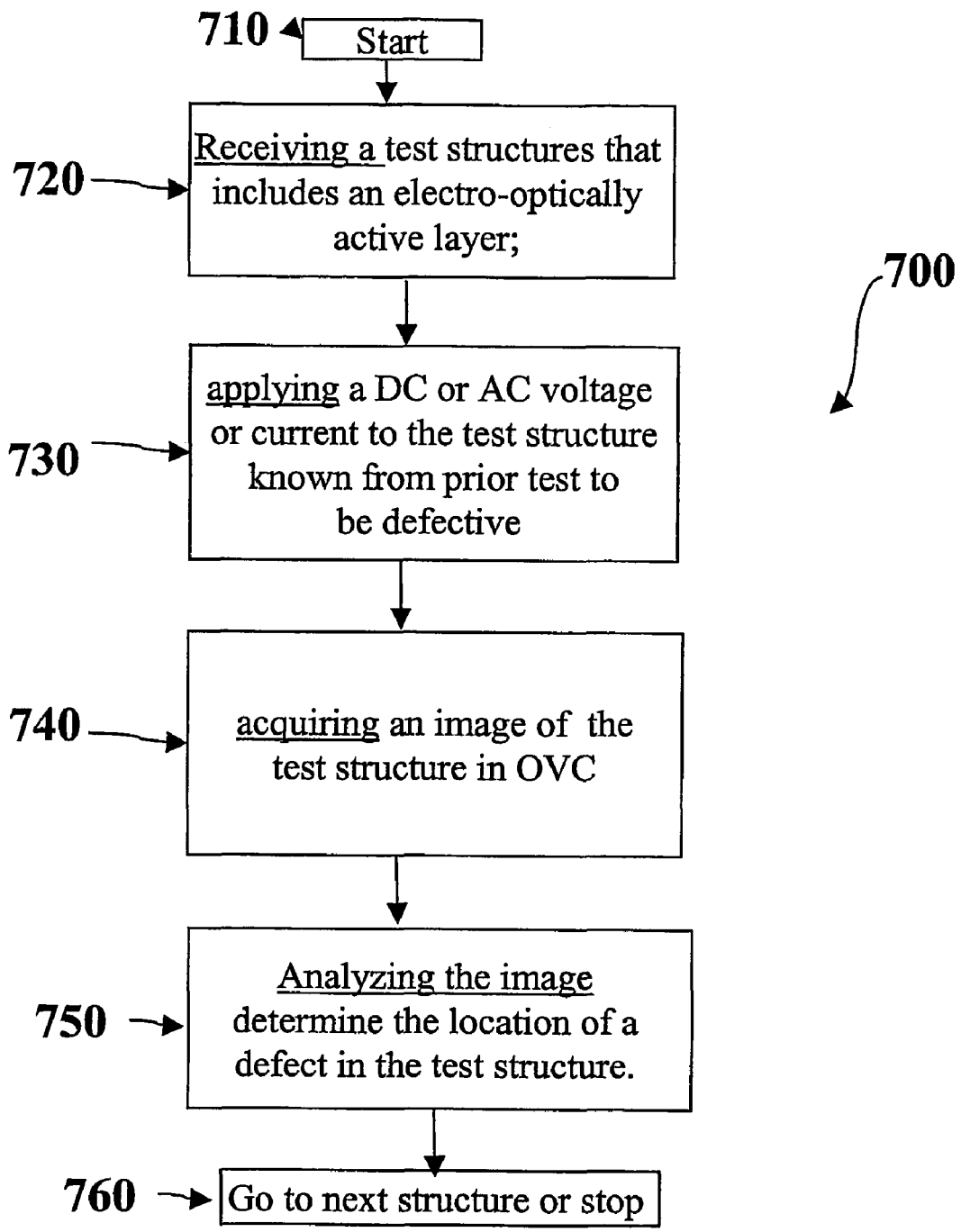

Note that the defect is typically located at (or near) the discontinuity in the gray level of the conductors that form the test structure. Note also that the discontinuity is present, even when the defect is a high resistance defect. In serpents and via chains, the magnitude of the discontinuity is typically proportional the resistance of the defect. FIG. 7 is a flow diagram of method 700 for defect localization. Method 700 includes: "start" step 710, step 720 of receiving a test structure that includes an electro-optically active layer, step 730 of applying DC or AC voltage or current to the test structure that is known to be defective, step 740 of imaging the test structure in optical voltage contrast mode, and step 750 of analyzing the image (tracking grayscale difference) to determine the location of a defect in the test structure. The method can be repeated for multiple test structures (as indicated by step 760 "go to next structure or stop loop").

Figure 8:
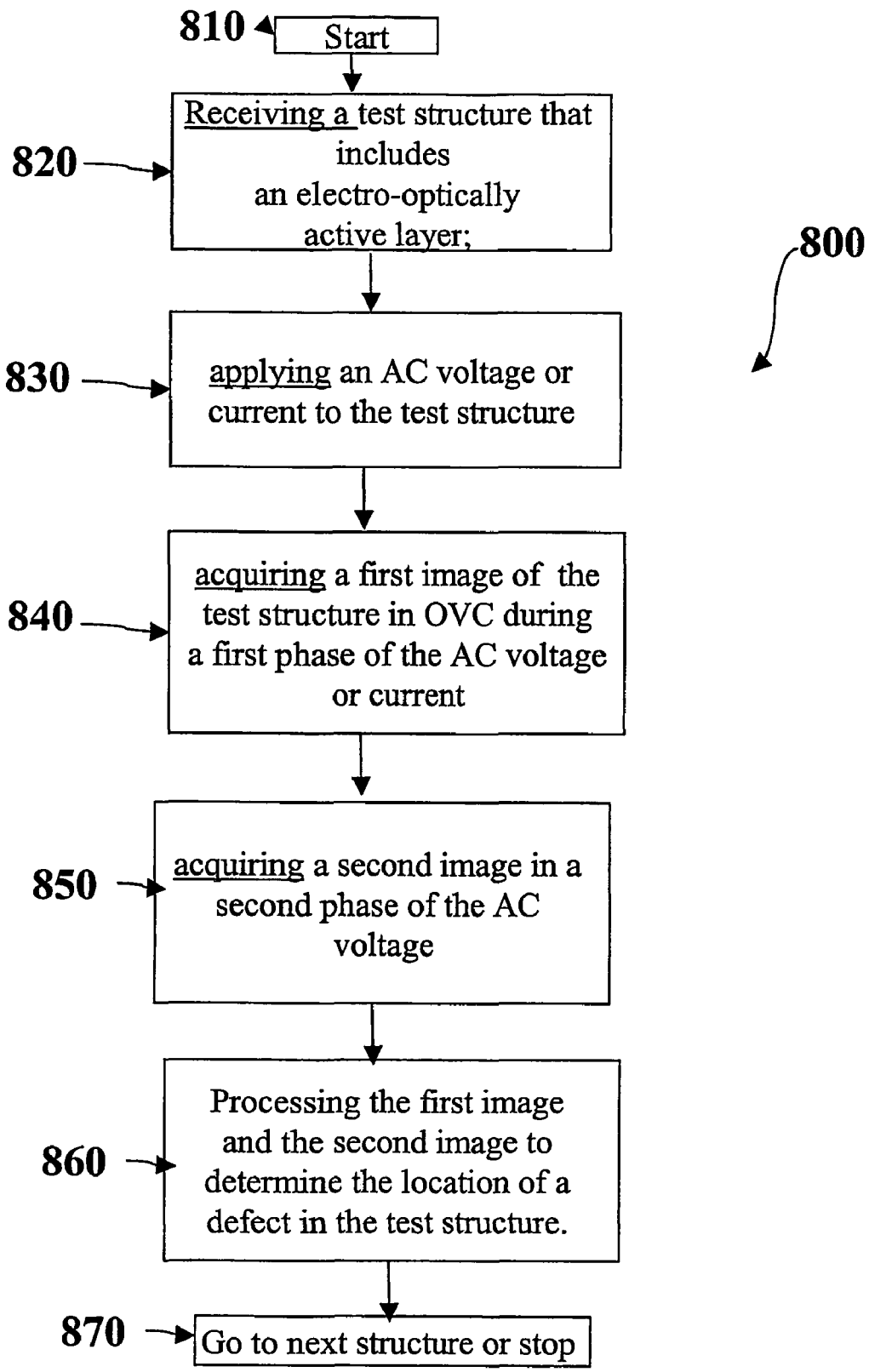

FIG. 8 is a flow diagram of method 800 for defect localization. Method 800 includes: "start" step 810, step 820 of receiving a test structure that includes an electro-optically active layer, step 830 of applying an AC voltage or current to the test structure that is known to be defective, step 840 of acquiring a first image of the test structure in optical voltage contrast mode, during a first phase of the AC voltage or current, step 850 of acquiring a second image of the test structure in optical voltage contrast mode, during a second phase of the AC voltage or current and step 860 of analyzing the first and second images to determine the location of a defect in the test structure. Step 860 may include comparing the pictures, generating a difference image and the like. Various methods for manipulating the pixels of each picture may be used. The method can be repeated for multiple test structures (as indicated by step 870 "go to next structure or stop loop"). It is further noted that more than two images of the same test structure can be acquired. Usually, the acquisition of multiple images improves the signal to noise ratio.

The alternating signal alternates at a relatively low frequency that may not exceed 100 Hz. An alternating signal can have an amplitude of about 5 volts.

Figure 9:
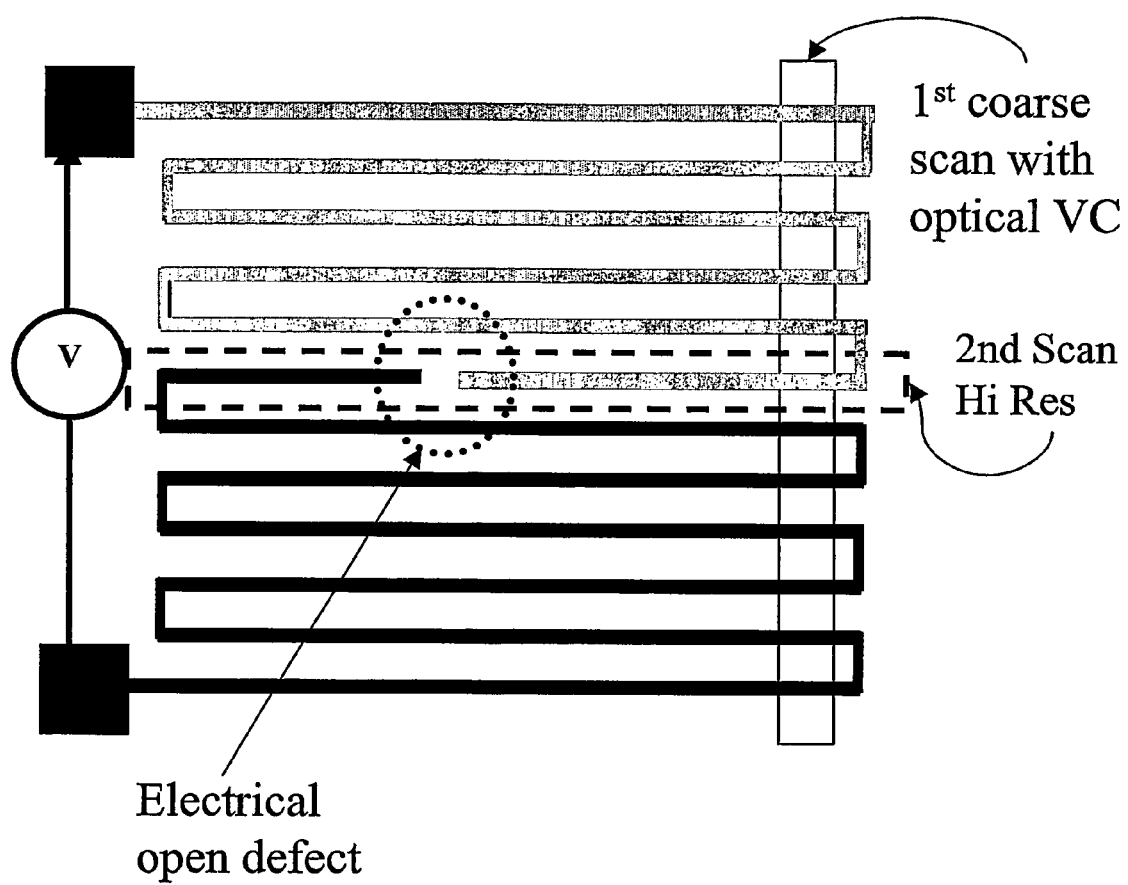
FIG. 9 illustrates a defective test structure that is imaged to provide a coarse image as well as a fine image of one of its portions, according to an embodiment of the invention.

FIG. 9 illustrates a test structure 400 that is inspected by a two step localization method that include a first coarse scan of the test structure that is followed by a finer scan. The test structure can be larger than the field of view of the imaging optics, thus multiple step and scan steps are required.

According to various embodiments of the invention: (i) the test structure can be backside illuminated with infrared illumination having a wavelength of about 1.06 microns; (ii) test structures include an electro-optically active substrate such as GaAs or the substrate can act as the electro-optically active layer; (iii) the electro-optically active material is birefringent, a polymer, DAN [4-(N,N-dimethylamino)-3-acetamidomitrobenzene], COANP [2-cyclo-octylamino-5-nitropyridine], PAN [4-N-pyrrolydino-3-acetaminomitrobenzene, MBANP [2-(alpha-methylbenzylanino)-5-nitropyridine], or liquid crystal; (iv) the electro-optically active material is disposed by spin-on, PVD, CVD or ALD; (v) the electro-optically active material is disposed such as to have a thickness that is substantially equal to a width of at least one conductor; (vi) the test structure is imaged with a resolution to detect defects comparable in size to a smallest dimension of a conductor of the test structure; and (vii) the resolution is selected in response to a dimension of at least one conductor.

The present invention can be practiced by employing conventional tools, methodology and components. Accordingly, the details of such tools, component and methodology are not set forth herein in detail. In the previous descriptions, numerous specific details are set forth, such as shapes of test structures and materials that are electro-optically active, in order to provide a thorough understanding of the present invention. However, it should be recognized that the present invention might be practiced without resorting to the details specifically set forth.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. A system for defect localization in a test structure, comprising:
   a stage configured to support and position the test structure within the system;
   means for illuminating an electro-optically active layer, wherein (i) the electro-optically active layer coats only a top surface of the test structure, (ii) said test structure includes a conductor, and (iii) the electro-optically active layer provides an indication about an electrical status of the conductor;
   a detector configured to detect light scattered or reflected from the electro-optically active layer;
   means for providing an alternating current electrical signal coupled to the conductor of the test structure, said alternating current electrical signal characterized by multiple phases and said means for providing further configured to synchronize phases of the alternating current electrical signal with image captures of the test structure; and a processor configured to (i) generate a first image of the test structure during a first phase of the electrical signal based on detection signals received from the detector, (ii) generate a second image of the test structure during a second phase of the electrical signal based on detection signals received from the detector, and (iii) process the first and second images in order to locate a defect in the test structure.

2. The system of claim 1, wherein the means for illuminating illuminates the test structure with a polarized light.

3. The system of claim 1, further adapted to report the location of the defect.

4. The system of claim 1, wherein an amplitude of the electrical signal is about 5 volts.

5. The system of claim 1, wherein the processor is further configured to generate a difference image between the first and second images.

6. The system of claim 1, wherein the electrical signal alternates at a frequency that ranges between 1-100 Hz.

7. The system of claim 1, wherein the system is adapted to image the test structure with sufficient resolution to detect defects comparable in size to a smallest dimension of the conductor of the test structure.

* * * * *